(12) United States Patent
Sales (10) Patent No.: US 8,661,922 B2
(45) Date of Patent: Mar. 4, 2014

(54) TOOL FOR SAMPLING MATERIAL IN A CONTAINER

(75) Inventor: Nick Sales, Birmingham (GB)

(73) Assignee: MMIC EOD Limited, West Midlands (GB)

( * ) Notice: Subject to any disclaimer, the term of this patent is extended or adjusted under 35 U.S.C. 154(b) by 405 days.

(21) Appl. No.: 13/119,174

(22) PCT Filed: Sep. 16, 2009

(86) PCT No.: PCT/GB2009/051200
§ 371 (c)(1),
(2), (4) Date: Mar. 15, 2011

(87) PCT Pub. No.: WO2010/032047
PCT Pub. Date: Mar. 25, 2010

(65) Prior Publication Data
US 2011/0167934 A1   Jul. 14, 2011

(30) Foreign Application Priority Data
Sep. 16, 2008   (GB) .................................. 0816895.7

(51) Int. Cl.
*G01N 1/10* (2006.01)
(52) U.S. Cl.
USPC ..................................... 73/864.74; 73/863.85
(58) Field of Classification Search
USPC .............................. 73/863.83, 863.84, 863.85
See application file for complete search history.

(56) References Cited

U.S. PATENT DOCUMENTS

| 5,704,383 | A | 1/1998 | Kammeraad et al. |
| 5,907,110 | A | 5/1999 | Garcia et al. |
| 6,065,488 | A | 5/2000 | Garcia et al. |
| 6,293,163 | B1 | 9/2001 | Johnston et al. |
| 7,000,546 | B1 | 2/2006 | Bender et al. |
| 2003/0101830 | A1* | 6/2003 | Wickland et al. .......... 73/863.85 |
| 2008/0134868 | A1 | 6/2008 | Goldman et al. |

FOREIGN PATENT DOCUMENTS

| CN | 2843538 Y | 12/2006 |
| GB | 2331241 | 5/1999 |
| WO | PCT/GB2009/051200 | 2/2010 |

\* cited by examiner

*Primary Examiner* — Hezron E Williams
*Assistant Examiner* — Paul West
(74) *Attorney, Agent, or Firm* — Wells St. John P.S.

(57) ABSTRACT

A sampling tool (100, 200) for use in obtaining a sample of material from within a container comprises a cutter shaft carrying a cutting head (1, 101), the shaft including a passage which has an inlet located at or towards the cutting head (1, 101), a drive mechanism which is adapted to cause the cutter shaft to rotate in a first direction in turn to cause the cutting head to cut a hole in wall of the container and expose the inlet to the material contained within the container, a flexible seal (3, 103) carried by the cutter shaft which is located so that with the inlet in contact with the fluid the seal extends at least partially through the hole, a clamp mechanism which is operable once the seal is located in the hole such that continued rotation of the cutter shaft pulls the cutting head (1, 101) back towards the hole to mechanically clamp the seal (3, 103) around the hole; and a self sealing connector which is in connection with an outlet of the passage and through which a sample may be withdrawn into a suitable receptacle by drawing it through the passage.

15 Claims, 6 Drawing Sheets

TOOL FOR SAMPLING MATERIAL IN A CONTAINER

CROSS REFERENCE TO RELATED APPLICATION

This application is a 35 U.S.C. §371 of and claims priority to PCT International Application Number PCT/GB2009/051200 (Publication No. WO 2010/0032047 A2), which was filed 16 Sep. 2009 (16.09.09), and was published in English, and this application claims priority to GB Patent Application No. 0816895.7 which was filed 16 Sep. 2008 (16.09.08), and the teachings of which are incorporated herein by reference.

This invention relates to improvements in sampling tools for use in withdrawing a sample of a material (gas or liquid or paste or gel or powder or other material or a combination of different materials) from within a target container substantially without exposing a user or the environment to the contents of the container.

It is widely known that no non-invasive technique can precisely establish the contents of all sealed containers. There are, however, several occasions in which it may be essential to establish what is inside a container without exposing the contents to atmosphere. The container may be suspected to contain hazardous material such as toxic industrial chemicals. In order to decide how to deal with the container the contents may need to be analysed before it is moved or opened.

Tools that allow a user to sample the contents of a sealed container are known in the art. An example of a tool that can do this is disclosed in U.S. Pat. No. 6,065,488. The fluid sampling tool disclosed can be used in combination with a rotary hand held drill to bore a hole in a container, insert a valve and seal the bore hole. The tool collects a fluid sample from the hole without exposing the operator or the environment to the contents or to swarf produced during the boring of the hole. The seal is formed by capping the hole with a liquid sealant which is held in a reservoir in the tool and which is then allowed to cure once the sample has been taken.

One problem with that prior art tool which may be addressed by an embodiment of the invention is that it may be slow to use as the sealant must be given time to cure. In some instances this may make it unsuitable.

According to a first aspect the invention provides a sampling tool for use in obtaining a sample of material from within a container, the tool comprising:
a cutter shaft carrying a cutting head, the shaft including a passage which has an inlet located at or towards the cutting head,
a drive mechanism which is adapted to cause the cutter shaft to rotate in a first direction in turn to cause the cutting head to cut a hole in wall of the container and expose the inlet to the material contained within the container,
a flexible seal carried by the cutter shaft which is located so that with the inlet in contact with the fluid the seal extends at least partially through the hole,
a clamp mechanism which is operable once the seal is located in the hole such that continued rotation of the cutter shaft pulls the cutting head back towards the hole to mechanically clamp the seal around the hole; and
a self sealing connector which is in connection with an outlet of the passage and through which a sample may be withdrawn into a suitable receptacle by drawing it through the passage.

The clamp mechanism may be so arranged that drilling and clamping can be performed whilst rotating the drive mechanism (and shaft) in a single direction only, i.e. in the first direction.

In more detail, in one particularly preferred embodiment the sampling tool may comprise: a hollow cutter shaft having the inlet to the passage at the cutting head end and an outlet located at the other end of the shaft, the clamp mechanism comprising a clamp member threaded onto a thread which extends over a length of the cutter shaft, preferably located between the seal and the outlet, the clamp member having a complimentary threaded bore to the thread of the shaft.

It may also include a sleeve which surrounds the cutter shaft. The sleeve may have an end portion which can be pressed against the wall to steady the device in position during cutting. This sleeve may be removable.

The sleeve may have a first inner portion within which the clamp member is located prior to cutting the hole within which the clamp member can freely rotate together with the cutter shaft and a second inner portion into which the clamp member is received when the seal is positioned in the hole and which prevents rotation of the clamp member relative to the sleeve upon further rotation of the cutter shaft.

An expander my be located between the cutter head and the seal which functions to expand the seal within the hole as the cutting head is pulled back towards the hole, causing the seal to clamp around the inner perimeter of the hole and, perhaps, also onto the region of wall around the hole inside the container. This expander may simply be formed by ensuring the outer diameter of the cutter head is greater than the internal diameter of the seal so that as it is pulled towards the seal it causes the seal to deform.

In an alternative, or in additional to, the clamp member being prevented from rotating by entering a second inner portion of a sleeve, the seal may taper outwards towards the end nearest the outlet so that the diameter of the seal at a point close to the cutting head is equal to or less than that of the cutting head and at a point nearer the outlet is greater than that of cutter head whereby in use once the cutter head has cut through the wall the seal may be jammed firmly into engagement with the inner peripheral wall of the hole so as to prevent further rotation of the seal and the clamp portion. This can eliminate the need to use the sleeve to prevent the clamp member from rotating once the seal is in place, the operation of the assembly otherwise remaining substantially the same.

The thread of the cutter shaft may be of opposite hand to the direction in which the cutter shaft is rotated during operation.

The thread preferably has a left hand thread so that the drive mechanism can be operated by a conventional drill that rotates the cutter shaft in a clockwise direction (a conventional forward direction for most off the shelf drills) with both cutting and clamping being achieved by operating the drill in only a single direction. Of course, if it is to be used with a drill that turns anti-clockwise a right hand thread could be used. This will require a user to drill in one direction to form the hole and then reverse the drill to clamp the seal in place.

The sleeve may have a cylindrical bore along its first portion of its length which has a diameter greater than the diameter of the clamp member so that the clamp member can freely move along it as the cutter shaft moves with substantially no relative movement between them.

The second portion may be shaped to co-operate with the clamp member so that the clamp member when in a correct orientation will slide into the second portion but cannot then rotate. For example, the sleeve may have a cylindrical bore all along its length with a set of three or more angularly spaced screws protruding into the bore in the region of the second portion so as to prevent the nut rotating when it lies within the screws in the second portion. This is advantageous as the screws can be wound in and out precisely to suit the clamp member.

In a most preferred arrangement the clamp member is a nut. It may have a hexagonal or octagonal outline.

Alternatively, the second portion of the bore may be hexagonal or octagonal or otherwise shaped to match the nut rather than cylindrical although this is harder to produce.

As already suggested, this clamp member may be prevented from rotating by the action of wedging it into the hole that has been formed.

A liner may be provided within the sleeve which is capable of absorbing at least a small amount of any material from within the container that is released past the seal during drilling or sealing. This may, for example, comprise a portion of activated charcoal.

An additional compressible seal may also be provided within the sleeve on the face of the clamp member that faces the surface of the container and which, with the tool being used to clamp provides an additional seal onto the outer surface of the container around the nut and hole.

The device may include a syringe which is releasably connected to the bore in the hollow cutter through the self-sealing connector. It preferably is connected as part of the tool prior to and then during cutting and sealing. It may be connected by a coupling which includes a lock ring that in a rest position prevents release of the coupling and automatically releases the coupling as the user pulls back on the drive mechanism after the seal has been formed and after the syringe has been filled. The drive mechanism may be configured so that pulling back on the drive mechanism (away from the cutting head) initially pulls the barrel of the syringe away from the plunger to draw a sample into the syringe and then continued pulling on the barrel pulls on the plunger which is connected to the connector and which draws on the lock ring to a release position in which the coupling and therefore the syringe is released.

When the syringe is removed the self-sealing connector should remain connected to the cutter shaft to provide a leak free and, optionally, reusable seal through which further samples can be withdrawn or other actions performed.

The coupling may comprise a male and a female part, one of which is sealed to the cutter shaft and the other sealed to the syringe so that on separation no fluid can leak from either the shaft or the syringe.

The sleeve may be sized so that it can be easily gripped in a hand and pressed against the wall of the container around a point where the hole is to be drilled. This enables an operator to steady the device whilst cutting the hole and forming the seal and also helps to trap any swarf produced during cutting. It may be provided with ribs around its outer surface.

A seal may be provided around the edge of the sleeve which contacts the wall. The sleeve may be provided with ribs around its outer surface to make it easier to grip securely. A handle which extends at right angles from the sleeve in the manner of a conventional hand held drill may be provided. One or more conformable vacuum pads may be provided which enable the sleeve to be affixed temporarily to the wall through which the hole is to be cut. The pads may be connected to suitable valves for connection to a compressor to enable them to be evacuated at least partially to provide the required suction onto the wall. In an alternative the sleeve could be fixed in place using fast cure adhesives, or perhaps using one or more magnets which are secured to the sleeve. The magnets and/or vacuum pads may be removably secured to the sleeve, perhaps through a hinged adapter.

The apparatus of the invention therefore allows an opening to be cut in a surface of a container from which a sample is to be taken by first offering the end of the sleeve up to the surface and then rotating the drive mechanism whilst applying force to advance the cutter. Once the cutter has penetrated the surface the seal can be pushed into the hole made by the cutter. Once this is complete the nut will engage the part of the sleeve that stops it rotating, and further rotation of the shaft will cause it to be pulled back to push the expander into the seal due to the threaded engagement between the nut and the hollow cutter. Thus cutting and sealing can be achieved in one action using a simple device suitable for hand operation.

The drive mechanism may include a drive shaft which is so shaped that it can be secured to a hand drill and a connector which prevents relative rotation between the drive shaft and the cutter shaft. This may form part of the end of the barrel of the syringe.

The drive shaft may be hexagonal in cross section so that it can be fixed to the chuck of a hand drill very securely.

Alternatively the drive mechanism may be configured for connection to a device which allows remote control operation rather than use as a hand tool.

All parts of the tool which may be in contact with any substance in the container may be made from material that is resistant to corrosion. For example, parts may be made from one or more of stainless steel, Nylon or PTFE.

The seal may be composed of a homogenous material designed to withstand the corrosive actions of the container's contents. Examples of suitable materials would be Nylon or PTFE.

An alternative composite seal may be provided comprising a segmented rigid portion (perhaps of a metal being chosen for its strength and a degree of chemical resistance, for example a type of stainless steel) to add mechanical strength to the seal, this portion being overlain with a more flexible (and also chemically resistant) layer which may be composed of, for example, Nylon, PTFE, Viton or a generic Perfluoroelastomer material. This type of seal has been found to be advantageous when used on thin targets and/or those with a high internal pressure.

Any seal arrangement may be configured so that the sealing action occurs on the outside face of the target (by virtue of a conformable portion of the seal or a separate seal such as an o-ring coming into contact with the exterior target wall) as well as in the bore of the hole produced (by virtue of having an optional taper at the end of the seal as described above) and also on the inner wall of the target (by virtue of the expander portion of the drill deforming the seal onto the inner target wall).

A pilot guide, of smaller diameter than the cutting head, may be provided on the drilling axis which provides a centering mechanism during cutting in addition to the support provided by the sleeve. This may comprise a small diameter (relative to the cutting head) drill or pin which is biased away from the drive mechanism to protrude slightly beyond the cutting head by one or more springs. This bias presses the pilot guide into the wall and may reduce the tendency of the cutting head to wander during cutting of the wall.

The cutting head may comprise an annular cutter, or a conventional self-centering "twist" type drill bit. The former is preferred as it is possible to provide a cutting head which is more efficient, breaks through almost instantaneously across the full diameter of the cut thus reducing potential leakage of contents, and produces less swarf.

According to a second aspect the invention provides an invasive method of obtaining a sample of material from within a container using the sampling tool of the first aspect which comprises, subsequent to offering up the tool to the wall of the container through which the sample is to be removed:

rotating the cutter shaft so that the cutting head cuts a hole in the wall, moving the cutter shaft through the hole to insert the seal at least partially through the hole and to introduce the clamp member to the second portion of the sleeve, and further rotating the cutter shaft in the same direction so as to cause the cutting head to be pulled towards the clamp member thereby mechanically clamping the seal around the hole to make an airtight seal to the hole in the container.

The method may comprises continuously rotating the cutter shaft in one direction throughout all stages of the method set out hereinbefore so that cutting and sealing occurs in a continuous operation.

The method may comprise fitting a part of the drive mechanism to the chuck of a hand held drill and operating the drill to rotate the cutter. As mentioned before it may be fitted to a device that allows it to be used remotely from a user under remote control.

The method may further comprise drawing a sample through the cutter shaft into the syringe and subsequently removing the syringe with the sample. The sample may then be taken away for analysis.

There will now be described, by way of example only, one embodiment of the present invention with reference to the accompanying drawings of which.

Figure 1:
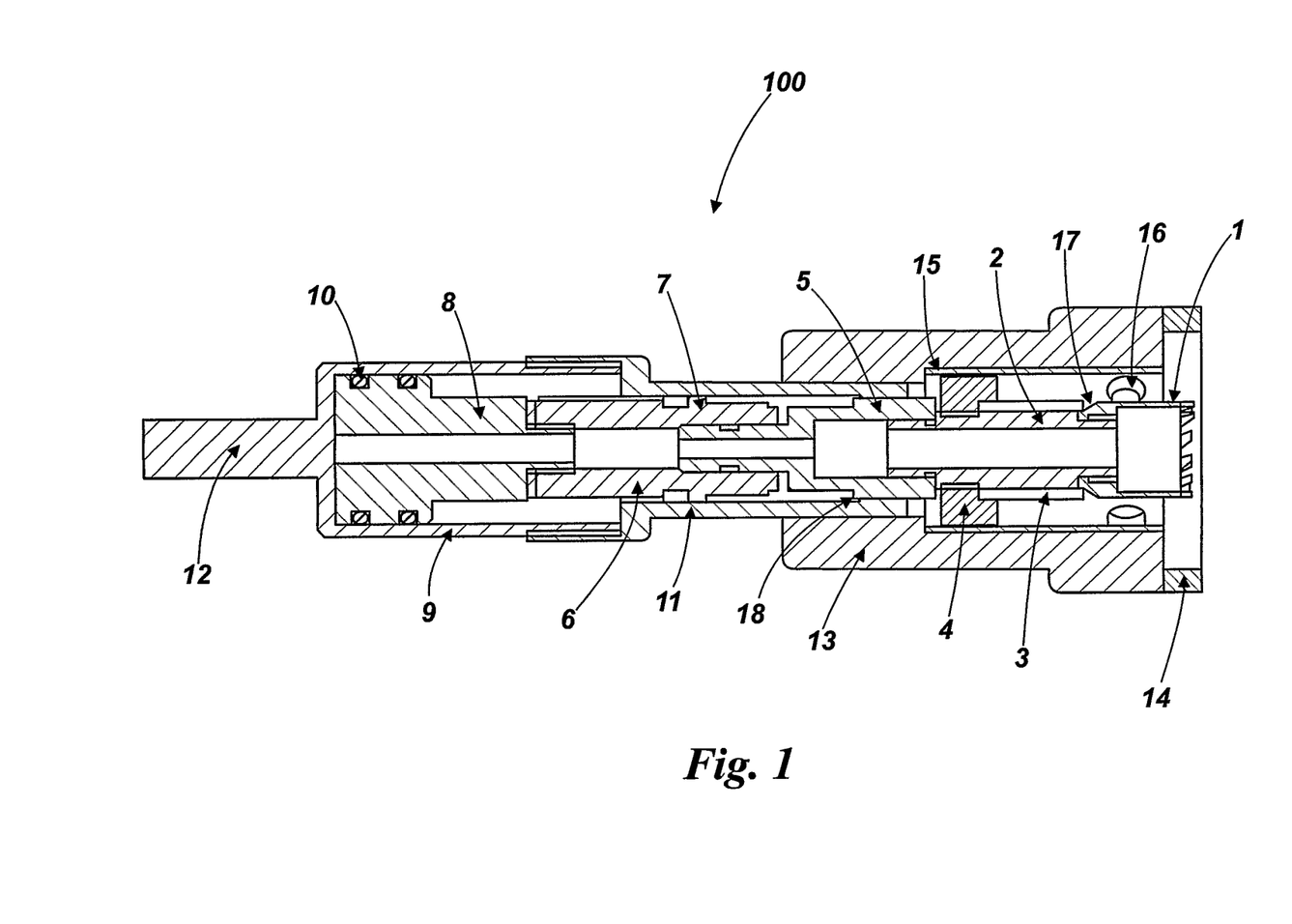
FIG. 1 is a cross sectional view of an embodiment of a sampling tool according to the invention.
Figures 2, 3:
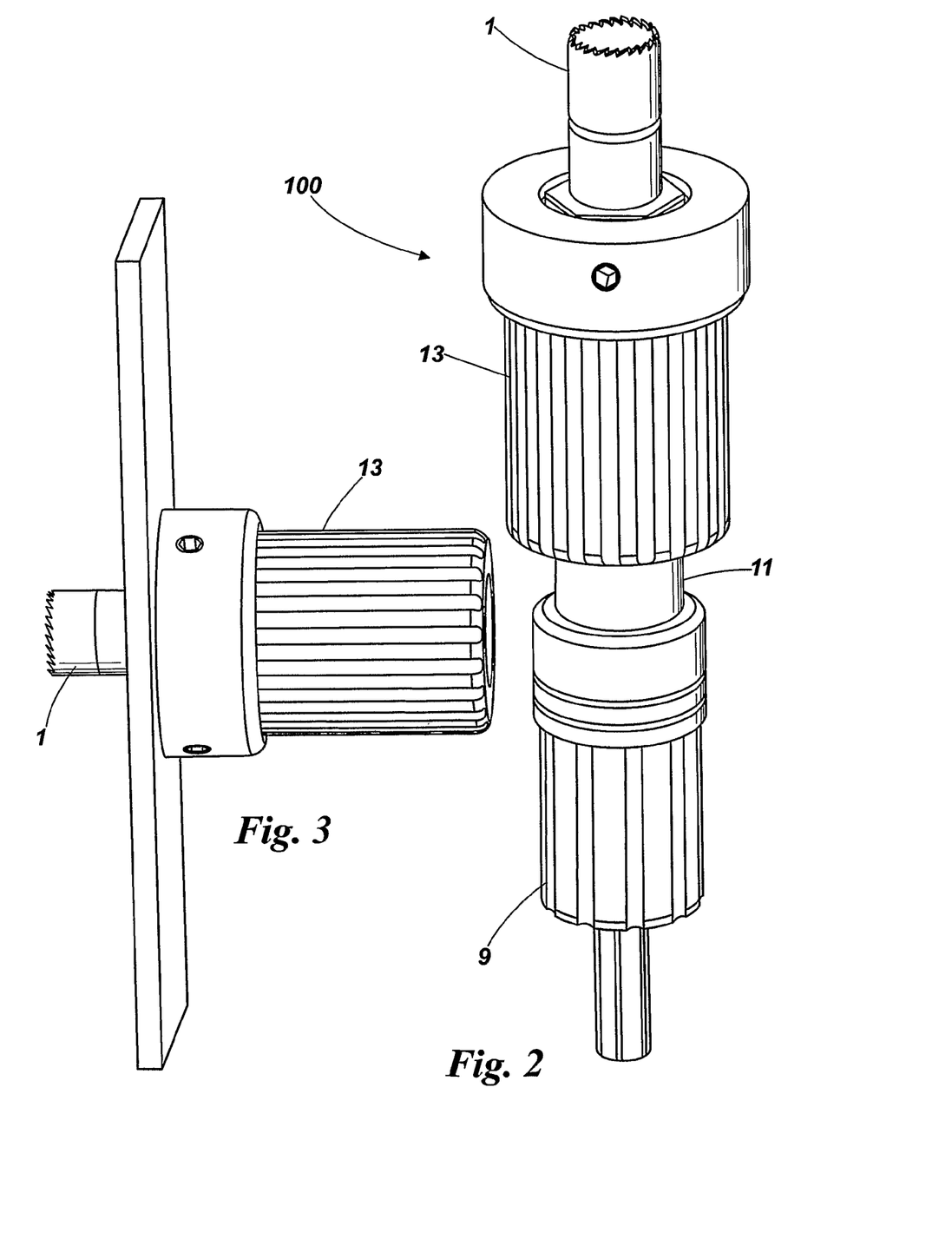
FIG. 2 is a perspective view of the embodiment of the invasive sampling tool of FIG. 1.
FIG. 3 shows the tool installed in a wall of a target container after the seal has been formed and the syringe withdrawn.
Figure 4:
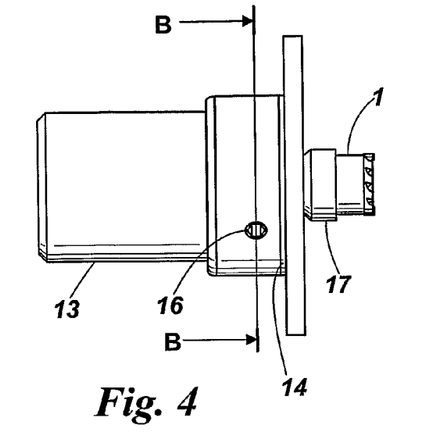
FIG. 4 shows in side elevation the device partially inserted after the cutter has penetrated the wall of the container.

As shown in FIG. 1, a sampling device is provided which can be fitted into a standard hand held drill and used to form a hole in, and seal the hole, in a target container whose contents are to be sampled. It is intended to be quick and simple to use and can cut the hole and form the seal in a single continuous operation of the hand drill by rotating in only a single direction. During a first part of the rotation the hole is cut, and thereafter on continued rotation the hole is mechanically sealed.

The device comprises an elongate cutting shaft which carries at one end an annular (hollow) cutter head 1 which is used to penetrate the wall of the item to be sampled (the target). The outer diameter of the head corresponds to the outer diameter of the hole to be cut. In this example the head has a diameter of 10 mm and comprises a ring of saw teeth which will cut a 10 mm bore hole.

The cutter head is affixed to the cutting shaft which forms part of a cutter back-end 2. A short distance from the end of the shaft at which the cutter head is provided there is an annular seal 3 which may be composed of a chemically resistant material. This seal is a tight fit around the shaft so that it can be pushed through the hole formed by the cutter head. It has the same or very slightly smaller diameter as the cutter head. Between this seal and the back of the cutter head (that side facing the seal) is an expander comprising a frusto-conical form which has its narrow part in contact with an edge of the seal.

The outside of the cutter back-end is threaded to accept a left-hand thread nut 4.

The bore of the cutter shaft 1 communicates with a male zero-drip self-sealing coupler 5 (which may be a suitable COTS [Commercial Off the Shelf] item) which is threaded onto the rear of the drill. This component couples to a female zero-drip self-sealing coupler 6 (which may be a suitable COTS [Commercial Off the Shelf] item), the two being released from each other by a sliding collar arrangement 7.

The female coupler is threaded onto a syringe piston 8 which forms a gas-tight sliding seal in the bore of a syringe barrel 9 utilising O-rings 10 which are composed of a chemically resistant material.

A threaded end-cap 11 is affixed to the end of the syringe, its bore being a sliding fit over 6 and 7. A hexagonal void at the end of 11 is a sliding fit over an external hexagonal portion of 5 such that rotation of barrel 9 is transmitted through end cap 11 and thence to the coupler 5 resulting in rotation of the cutter shaft 2. This cap, together with the syringe barrel and coupler therefore define a drive mechanism.

A drive-shaft 12 secured to the end cap in line with the cutter shaft 2 permits the entire assembly described so far to be rotated at a range of speeds using (for example) a COTS [Commercial Off the Shelf] hand-drill.

A sleeve located around the cutter shaft defines a hand-hold 13 acts to stabilise the drilling operation. It carries a peripheral seal 14 which may be composed of a chemically resistant material. This acts both to increase friction between the target and the hand-hold during drilling, and to trap swarf and any target contents released during drilling. In use the sleeve seal 14 is pushed onto the surface of the target before rotating the drive mechanism. The sleeve 13 may be lined with a chemically resistant and absorbent material 15 to further absorb any target contents released.

Figure 5:
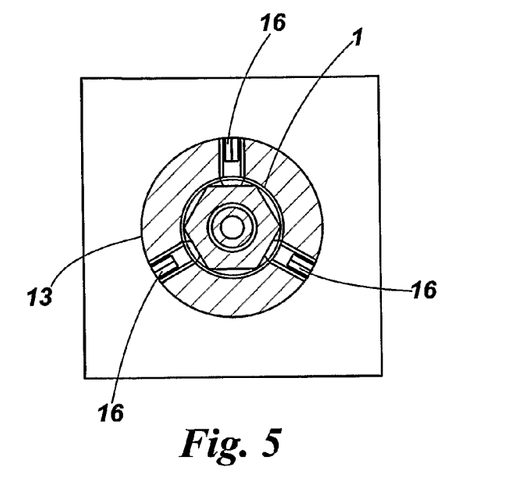
FIG. 5 shows a cross section on B-B of the device of FIG. 4.

A first portion of the inside of the sleeve 13 is sized such that as the cutter shaft rotates the nut 4 is able to rotate with it (no relative rotation between nut and shaft 2). The nut sits in this portion as the cutter is cutting. Three lock-screws 16 are radially arranged at 120 degree intervals around the bore of the sleeve 13 nearer the cutter head. As shown in FIG. 5, the relative positioning of these screws 16 is such that the nut 4 fits between them when the cutter has been pushed out of the sleeve 13 through the hole it has cut in the target wall. With the nut 4 so located it is prevented from rotating in the sleeve 13. Any continued rotation of the shaft causes the nut 4 to climb the shaft towards the cutter head, and because the nut 4 cannot move relative to the sleeve this effectively pulls the cutter head 1 back onto the seal and presses the nut towards the surface of the target. This in turn drives the frusto-conical expander 17 between the inner wall of the seal and the cutter shaft and expanding the seal onto the hole in the target. This enables a seal to be formed on a range of wall thicknesses from 1 mm to 10 mm and in tests the seal has been shown to be able to resist pressures up to 60 psi (4 bar). Through the choice of alternative seal materials higher pressures could be accommodated, and using different size cutter heads and seals other wall thicknesses can also be handled. An additional seal (for example an O-ring) may be present on the face of the nut which impacts the target in order to further improve the seal produced.

In use, the assembly is placed against the target and drilling commences. The cutter head is rotated and light pressure applied to cut into the target forming a hole. Once the cutter head 1 breaks through the target wall the seal 3 enters and seals the bore of the hole produced, being of the same diameter. As the cutter shaft continues to advance the nut 4 passes into the channel created by the screws 16 and is prevented from freely rotating within the sleeve 13, instead rotating along the threads of cutter shaft 2. This causes compression of the seal 3 against the inside wall of the target by the expander 17, resulting in a sealing action of the hole previously produced by 1.

Once sealing is complete the syringe is withdrawn away from the target. Target contents are aspirated through the bores of 1, 5, 7 and 8 by the vacuum produced by this action within the syringe barrel 9.

Figure 6:
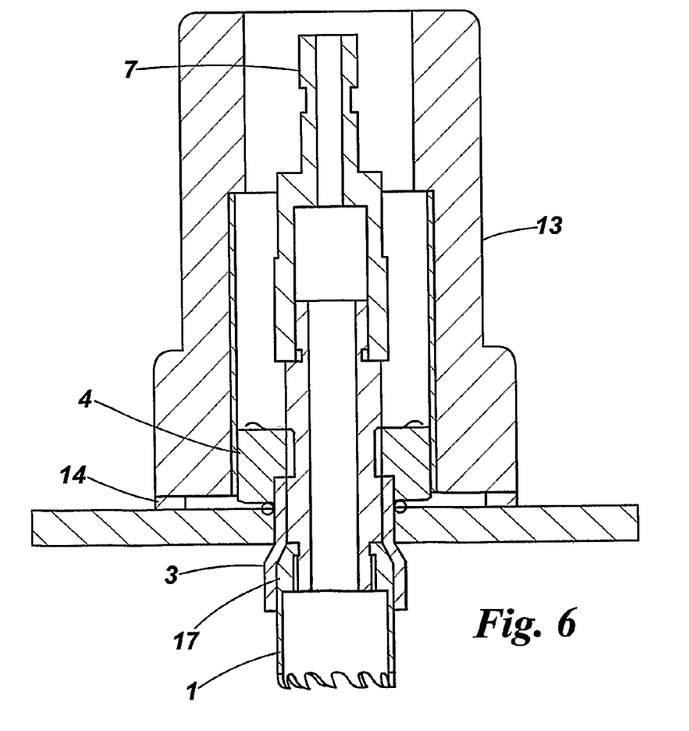
FIG. 6 shows in cross section the device after the cutter has been sealed to the wall following further rotation of the drive shaft.

Once the piston has reached the end of its travel, a release shoulder 18 impinges on a lock collar 7 and allows the parts of the connector 5 and 6 to de-couple, thus freeing the assembly (now containing a sample of target contents) from the target as shown in FIG. 6.

A sleeve of absorbent material may be present within the hand-hold in order to absorb any leakage produced during the drilling process.

Figure 7:
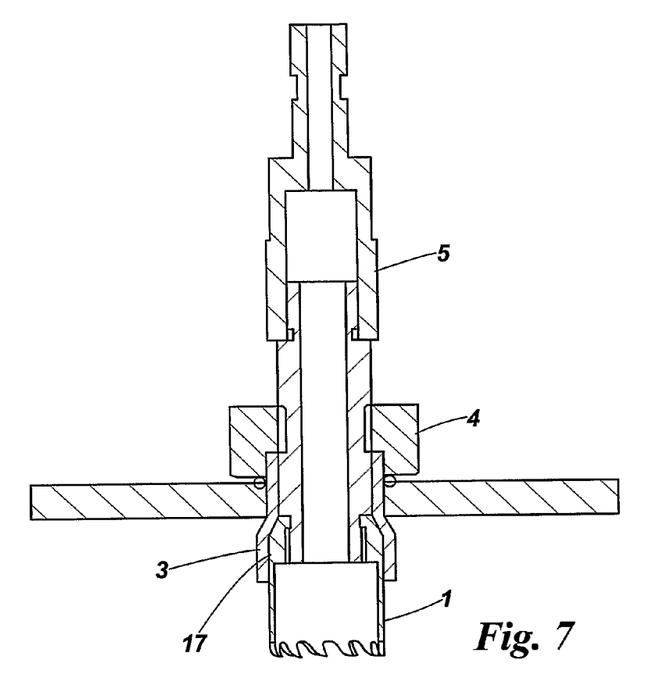
FIG. 7 shows in cross section the cutter and seal part of the device left in the wall of the container after removal of the syringe section.
Figure 8:
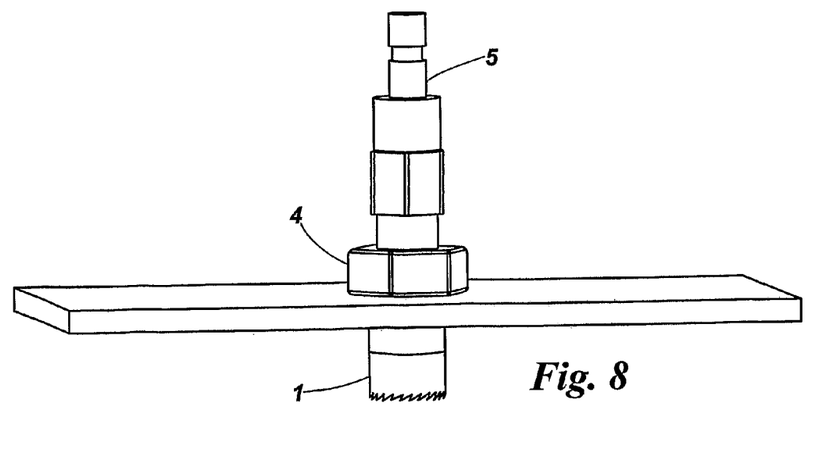
FIG. 8 is a perspective view of the apparatus in place with the guide sleeve removed.

Repeat sampling or other procedures (including the introduction into, or removal from, the target of further material) may now be performed by coupling suitable apparatus to the coupler 5 which remains in the target as shown in FIG. 7 and FIG. 8. The outer sleeve 13 may at this time be removed as shown.

Figure 9:
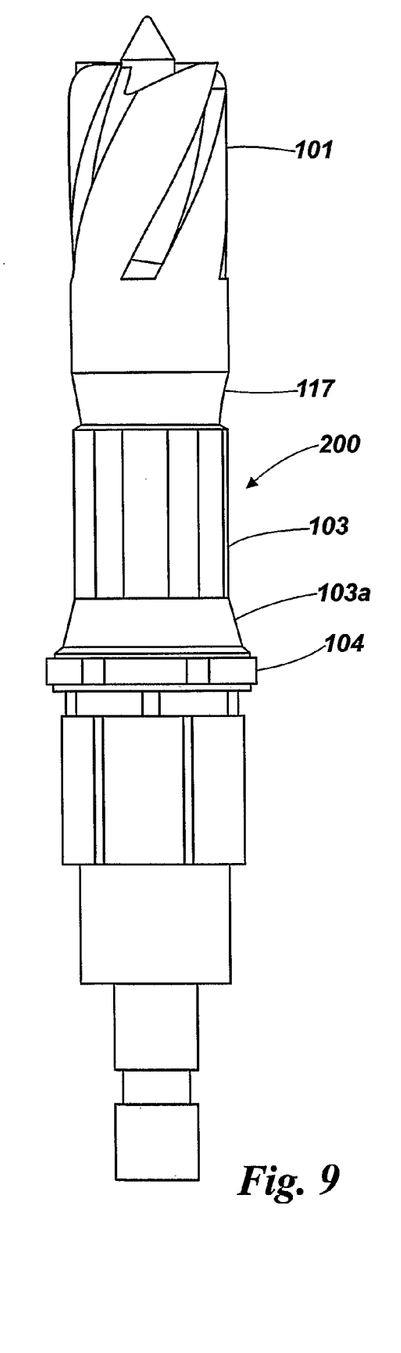
FIG. 9 is a view in side elevation of a second embodiment of a sampling tool according to the invention.
Figure 10:
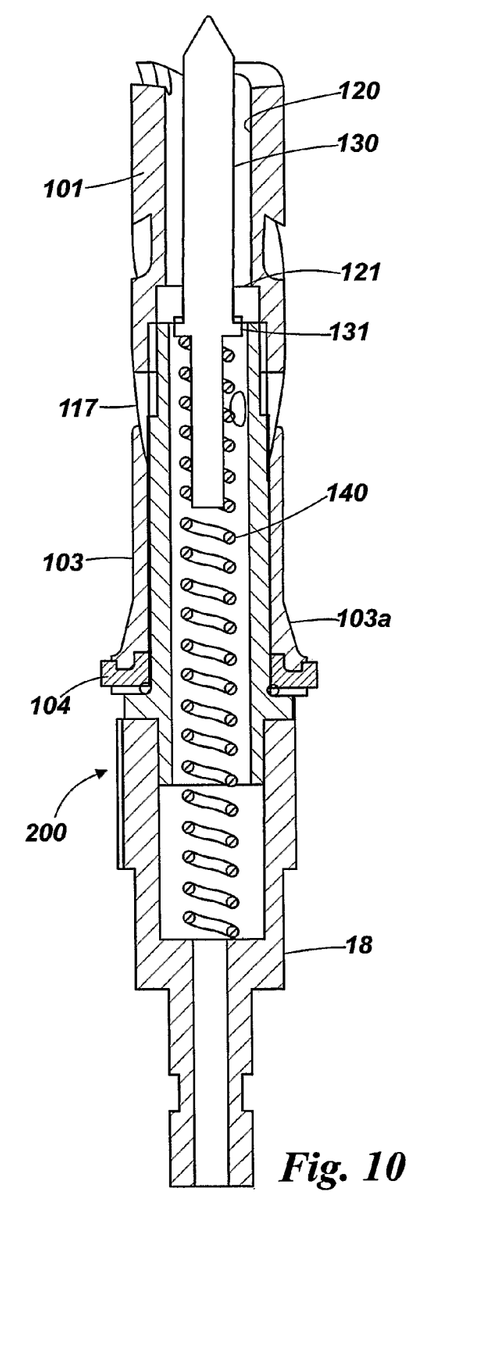
FIG. 10 is a cross sectional view of the tool of FIG. 9.
Figure 11:
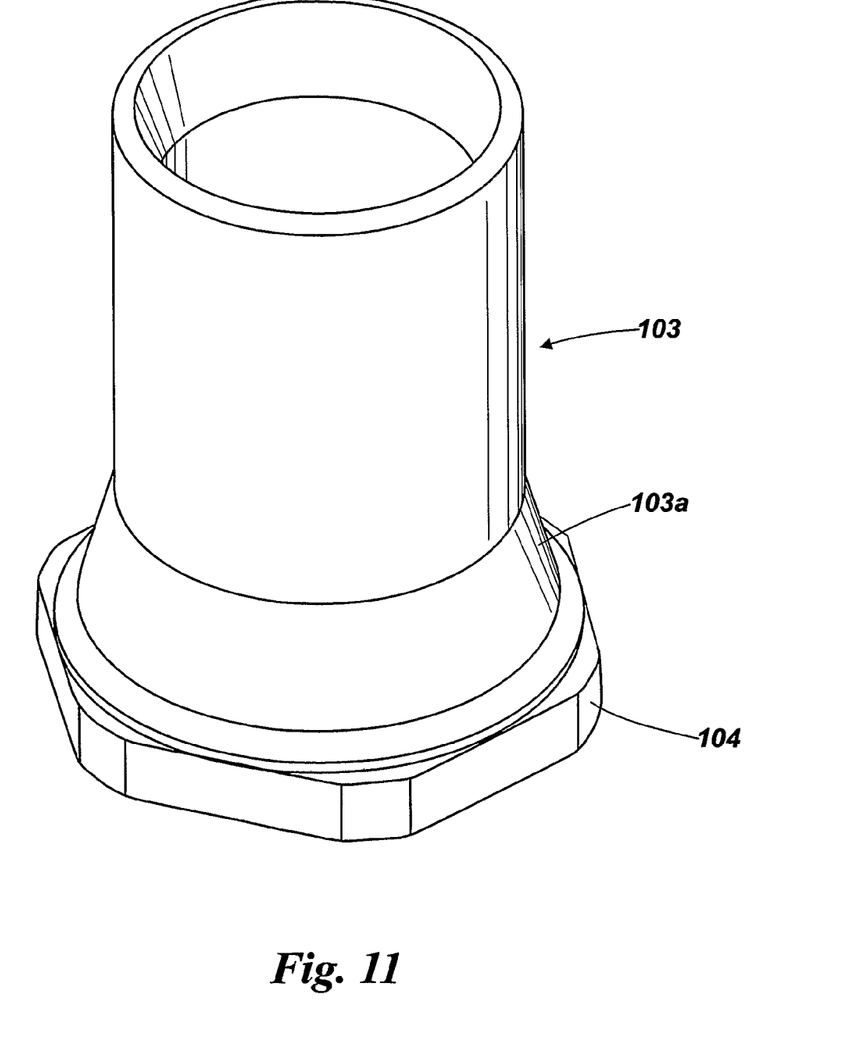
FIG. 11 is a perspective view of the tapered seal used in the tool of FIG. 9.

A second embodiment of a sampling tool 100 in accordance with the invention is illustrated in FIGS. 9 to 11 of the accompanying drawings.

This is substantially the same as the first embodiment in many respects, and elements which are the same have been omitted for clarity. The tool differs in the shape of the cutting head and the seal, and this impacts on the manner in which the seal is tightened into the hole in the target.

The cutter head 101 is now in the form of a self centering type drill bit, rather than an annual cutter. The drill bit has a bore 120 along the drilling axis which is open at the end of the cutting head, and within this bore 120 is located a pilot guide comprising a spring loaded pin 130, biased away from the drive mechanism end of the tool by a coil spring 140. This pin 130 helps to self-centre the tool during drilling. The pin 130 is prevented from being pushed out of the bore 120 by an annular lug 131 on the pin which engages an inwardly projecting annular lip 121 in the bore.

The seal 103 is shown on its own in detail in FIG. 11 of the accompanying drawings. It differs from that of the first embodiment because it tapers outwards at its end distal from the cutting head 101. At its widest this tapered portion 103a has a greater diameter than the cutting head, and as such has a greater diameter than the hole that the cutting head will form. The tapered portion of the seal 103 is secured against rotation to a clamp member in the form of a nut 104, which is threaded to the cutting shaft in a similar manner to nut 4 of the first embodiment. The nut may be integrally formed with the seal.

In use, the pin 130 is presented to the wall through which a hole is to be cut, and the cutting head 101 is then rotated using a drill attached to the tool whilst the cutting head is pressed to the wall. The cutting head 101 cuts through the wall, and on break through continued application of pressure causes the seal 103 to enter the hole. Because of the taper portion 103a being larger in diameter than the hole that has been drilled the seal 103 jams in place in the hole preventing further rotation of the seal. Because the seal 103 is secured to the nut 104, continued rotation of the cutter shaft causes the nut 104 to move along the cutter shaft in a similar manner to that of the first embodiment. This draws the cutter head 101 back towards the hole, forcing an expander 117 into the seal 103 and together with the nut 104 clamping the seal 103 to the hole.

The invention claimed is:

1. A sampling tool for use in obtaining a sample of material from within a container having a wall, the tool comprising:
   a cutter shaft carrying a cutting head, the shaft including a passage which has an inlet located at or towards the cutting head,
   a drive mechanism which is adapted to cause the cutter shaft to rotate in a first direction in turn to cause the cutting head to cut a hole in the wall of the container and expose the inlet to the material contained within the container,
   a flexible seal carried by the cutter shaft which is located so that with the inlet in contact with the material the seal within the container extends at least partially through the hole,
   a clamp mechanism which is operable once the seal is located in the hole such that continued rotation of the cutter shaft pulls the cutting head back towards the hole to mechanically clamp the seal around the hole; and
   a self sealing connector which is in connection with an outlet of the passage and through which a sample of the material may be withdrawn into a suitable receptacle by drawing it through the passage.

2. A sampling tool according to claim 1 in which the clamp mechanism is arranged so that drilling and clamping can be performed whilst rotating the drive mechanism in a single direction only.

3. A sampling tool according to claim 1 which further includes an expander located between the cutter head and the seal which functions to expand the seal within the hole as the cutting head is pulled back towards the hole, causing the seal to clamp around the inner perimeter of the hole.

4. A sampling tool according to claim 1 wherein said cutter shaft is hollow and has the inlet to the passage at the cutting head end and an outlet located at the other end of the shaft, the clamp mechanism comprising a clamp member threaded onto a thread which extends over a length of the cutter shaft located between the seal and the outlet, the clamp member having a complimentary threaded bore to the thread of the shaft.

5. A sampling tool according to claim 4 which includes a sleeve which surrounds the cutter shaft, the sleeve having an end portion which can be pressed against the wall to steady the device in position during cutting in which the sleeve has a first inner portion within which the clamp member is located prior to cutting the hole within which the clamp member can freely rotate together with the cutter shaft and a second inner portion into which the clamp member is received when the seal is positioned in the hole and which prevents rotation of the clamp member relative to the sleeve upon further rotation of the cutter shaft.

6. A sampling tool according to claim 5 in which a liner is provided within the sleeve which is capable of absorbing at least a small amount of any material from within the container that is released past the seal during drilling or sealing.

7. An invasive method of obtaining a sample of material from within a container using the sampling tool of claim 5 which comprises, subsequent to offering up the tool to the wall of the container through which the sample is to be removed:

rotating the cutter shaft so that the cutting head cuts a hole in the wall, moving the cutter shaft through the hole to insert the seal at least partially through the hole and to introduce the clamp member to the second portion of the sleeve, and further rotating the cutter shaft in the same direction so as to cause the cutting head to be pulled towards the clamp member thereby mechanically clamping the seal around the hole to make an airtight seal to the hole in the container.

8. A sampling tool according to claim 4 in which the seal tapers outwards towards the end nearest the outlet so that the diameter of the seal at a point close to the cutting head is equal to or less than that of the cutting head and at a point nearer the outlet is greater than that of cutter head whereby in use once the cutter head has cut through the wall the seal may be jammed firmly into engagement with the inner peripheral wall of the hole so as to prevent further rotation of the seal and the clamp member.

9. A sampling tool according to claim 4 in which the clamp member is a nut.

10. A sampling tool according to claim 1 in which a thread of the cutter shaft is of opposite hand to the direction in which the cutter shaft is rotated during operation.

11. A sampling tool according to claim 1 which includes a syringe which is releasably connected to the passage in the cutter shaft through the self-sealing connector by a coupling which includes a lock ring that in a rest position prevents release of the coupling and automatically releases the coupling as the user pulls back on the drive mechanism after the seal has been formed and after the syringe has been filled.

12. A sampling tool according to claim 1 in which the drive mechanism includes a drive shaft which is so shaped that it can be secured to a hand drill and a connector which prevents relative rotation between the drive shaft and the cutter shaft.

13. A sampling tool according to claim 1 in which the seal comprises a segmented rigid portion overlain with a more flexible chemically resistant layer.

14. A sampling tool according to claim 1 in which a pilot guide of smaller diameter than the cutting head, is provided on a drilling axis of the cutter shaft which provides a centering mechanism during cutting.

15. A sampling tool according to claim 14 in which the pilot guide comprises a small diameter drill or pin which is biased away from the drive mechanism to protrude slightly beyond the cutting head by one or more springs.

* * * * *